United States Patent [19]

Horii et al.

[11] 4,446,319
[45] May 1, 1984

[54] AMINOCYCLITOLS AND THEIR PRODUCTION

[75] Inventors: Satoshi Horii, Sakai; Hiroshi Fukase, Osaka, both of Japan

[73] Assignee: Takeda Chemical Industries, Ltd., Osaka, Japan

[21] Appl. No.: 371,988

[22] Filed: Apr. 26, 1982

[30] Foreign Application Priority Data

Apr. 28, 1981 [JP] Japan ................................. 56-64370
Sep. 11, 1981 [JP] Japan ................................ 56-144309

[51] Int. Cl.$^3$ ........................................... C07D 265/18
[52] U.S. Cl. ..................................... 544/92; 564/462; 560/115
[58] Field of Search .......................................... 544/92

[56] References Cited

U.S. PATENT DOCUMENTS 4,301,283  11/1981  Thorpe et al. ......................... 544/92
4,341,778  7/1982  Mentrup et al. .................. 544/92 X

OTHER PUBLICATIONS

Journal of Chem. Soc., Index pp. 746–747, (1972).
Chemistry Letters, pp. 135–138, 713–716, and 1559–1562, (1980).
Journal of Antibiotics, vol. 24,1, pp. 59–63, (1971).
Journal of Antibiotics, vol. 33,12, pp. 1575–1576, (1980).

*Primary Examiner*—Richard Raymond
*Attorney, Agent, or Firm*—Wegner & Bretschneider

[57] ABSTRACT

Novel aminocyclitols, namely the compounds of the formula

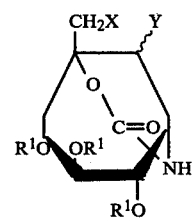

[I]

wherein X is hydroxyl group, a halogen or an acyloxy group; Y is hydrogen or a halogen; and $OR^1$ is an optionally protected hydroxyl group; and their production.

These aminocyclitols are important intermediates for preparing valiolamine having α-glucosidase inhibitory activity.

10 Claims, No Drawings

AMINOCYCLITOLS AND THEIR PRODUCTION

The present invention relates to novel aminocyclitols, which are intermediates for preparing the compounds having α-glucosidase inhibitory activity.

S. Horii et al. previously isolated, as a constituent of validamycin, an antibiotic, the compound of the formula,

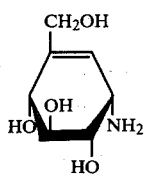

which was named "valienamine" (Y. Kameda and S. Horii; Journal of the Chemical Society; Chemical Communications, 1972, 746 to 747), and reported that valienamine possesses an action of suppressing the function of α-glucoside hydrolase (Y. Kameda et al., Journal of Antibiotics 33, 1575 to 1576 (1980)).

S. Horii et al. investigated an α-glycosidase inhibitory activity of various compounds which are similar to valienamine in chemical structure, and after extensive research, found that valiolamine, a compound of the formula

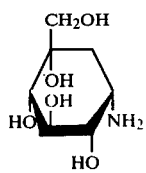

which was discovered and isolated from a culture broth of a strain of the genus streptomyces possesses αglucosidase inhibitory activity.

These findings were further followed by continued studies on how to prepare valiolamine by synthetic method, and as a result, the present inventors found that a compound of the formula

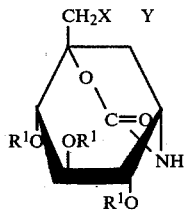 [I]

is an important intermediate for preparing valiolamine or its derivatives, which has culminated in the present invention.

In the above formula [I], Y is hydrogen or a halogen such as fluorine, chlorine, bromine and iodine; X is hydroxyl group, a halogen such as fluorine, chlorine, bromine and iodine or an acyloxy group represented by $-OR^3$ where $R^3$ is an acyl group such as alkanoyl groups of 1 to 5 carbon atoms exemplified by formyl, acetyl, propionyl and butyryl, and aromatic acyl groups exemplified by benzoyl. Hydroxyl group represented by X may be protected and represented by $OR^1$.

As the protective group for hydroxyl group represented by $R^1$, use is made of protective groups which are employed as hydroxyl protective groups in the chemistry of the sugars, such as acyl type protective groups, ether type protective groups and acetal or ketal type protective groups.

The acyl type protective groups include e.g. alkanoyl groups of 1 to 5 carbon atoms which may be substituted by benzoyl, trifluoromethyl, phenoxy or alkoxy of 1 to 5 carbon atoms; alkoxycarbonyl groups of 2 to 6 carbon atoms; benzoyl groups which may be substituted by nitro or phenyl; phenoxycarbonyl groups which may be substituted by nitro; and benzyloxycarbonyl group.

Examples of alkanoyl groups of 1 to 5 carbon atoms are as defined above regarding $R^3$. Examples of alkoxy of 1 to 5 carbon atoms or alkoxy in alkoxycarbonyl of 2 to 6 carbon atoms include methoxy, ethoxy, propoxy, butoxy, pentoxy etc.

More concretely, the examples of acyl type protective groups are formyl, acetyl, propionyl, isopropionyl, butyryl, pivaloyl, benzoylformyl, trifluoroacetyl, phenoxyacetyl, methoxyacetyl, ethoxyacetyl, propoxyacetyl, 3-benzoylpropionyl, methoxycarbonyl, ethoxycarbonyl, propoxycarbonyl, isobutyloxycarbonyl, pentyloxycarbonyl, benzoyl, p-nitrobenzyl, p-phenylbenzoyl, phenoxycarbonyl, p-nitrophenoxycarbonyl, benzyloxycarbonyl, etc.

The ether type protective groups include e.g. alkyl groups of 1 to 5 carbon atoms; alkenyl groups of 2 to 4 carbon atoms; trialkylsilyl groups of 3 to 6 atoms; and benzyl groups which may be substituted by alkoxy of 1 to 3 carbon atoms. The alkyl group may be substituted by phenyl or alkoxy of 1 to 5 carbon atoms.

More concretely, the ether type proptective groups are methyl, ethyl, tert-butyl, ethoxyethyl, allyl, trityl, trimethylsilyl, dimethylethylsilyl, benzyl, p-methoxybenzyl etc.

The acetal or ketal type protective groups have preferably 1 to 10 carbon atoms, and the protective groups include methylene, ethylidene, isopropylidene, methoxymethylene, ethoxymethylene, methoxyethylidene, dimethoxymethylene, cyclopropylidene, cyclopentylidene, cyclohexylidene, benzylidene, tetrahydropyranyl, methoxytetrahydropyranyl etc.

The above-mentioned hydroxyl-protective groups $R^1$ are not always required to be the same protective group in a series of reactions of the present invention, and the hydroxyl groups may be protected with protective groups which vary from reaction step to reaction step and are suited for their respective reaction, or may not be protected with any protective group.

Furthermore, specific examples of the aminocyclitols represented by the formula [I] include:
1. 9-bromo-6,7,8-trihydroxy-1-hydroxymethyl-3-oxo-2-oxa-4-azabicyclo[3.3.1]nonane;
2. 9-iodo-6,7,8-trihydroxy-1-hydroxymethyl-3-oxo-2-oxa-4-azabicyclo[3.3.1]nonane;
3. 9-chloro-6,7,8-trihydroxy-1-hydroxymethyl-3-oxo-2-oxa-4-azabicyclo[3.3.1]nonane;
4. 6,7,8-trihydroxy-1-hydroxymethyl-3-oxo-2-oxa-4-azabicyclo[3.3.1]nonane;
5. 6,7,8-triacetoxy-1-iodomethyl-3-oxo-2-oxa-4-azabicyclo[3.3.1]nonane;
6. 6,7,8-triacetoxy--acetoxymethyl-3-oxo-2-oxa-4-azabicyclo[3.3.1]nonane;
7. 6,7,8-triacetoxy-1-bromomethyl-3-oxo-2-oxa-4-azabicyclo[3.3.1]nonane;
8. 6,7,8-triacetoxy-1-chloromethyl-3-oxo-2oxa-4-azabicyclo3.3.1]nonane.

The compound of the formula [I] wherein X is halogen or hydroxyl, can be obtained by reacting a compound of the formula

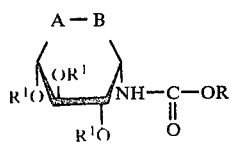 [II]

wherein —A—B— is

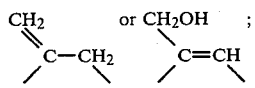 ;

R is an alkyl, aryl or aralkyl group; and OR$^1$ is an optionally protected hydroxyl group:
with a halogenating agent and, if necessary, removing the protective group.

An alkyl group represented by R means a straight-chain, branched saturated or unsaturated alkyl group of 1 to 10 carbon atoms, or a cyclic saturated or unsaturated alkyl group of 3 to 8 carbon atoms. Examples of the straight-chain, branched saturated alkyl group of 1 to 10 carbon atoms include methyl, ethyl, propyl, isopropyl, n-butyl, sec-butyl, isobutyl, tert-butyl, pentyl, hexyl, heptyl, octyl, nonyl, decyl etc. Examples of the straight-chain, branched unsaturated alkyl group of 1 to 10 carbon atoms include vinyl, allyl, isopropenyl, butenyl, pentenyl, hexenyl, heptenyl, octenyl etc.

Examples of the cyclic saturated alkyl group of 3 to 8 carbon atoms include cyclopropyl, cyclobutyl, cyclopentyl, cyclohexyl, cycloheptyl, cyclooctyl etc. Examples of the cyclic unsaturated alkyl group of 3 to 8 carbon atoms include cyclopropenyl, cyclobutenyl, cyclopentenyl, cyclohexenyl, cycloheptenyl, cyclooctenyl etc.

Examples of the aryl group represented by R include phenyl, naphthyl etc. Examples of the aralkyl group represented by R include benzyl, phenetyl, α-naphthylmethyl and 9-anthrylmethyl. Such alkyl, aryl and aralkyl groups may be substituted by 1 to 3 substituents such as lower alkyl groups of 1 to 4 carbon atoms e.g. methyl, ethyl, propyl and butyl, lower alkoxy groups of 1 to 4 carbon atoms e.g. methoxy, ethoxy, propoxy and butoxy, and others.

Further, the straight-chain, branched saturated or unsaturated alkyl of 1 to 10 carbon atoms may be substituted by cyclic saturated or unsaturated alkyl group of 1 to 10 carbon atoms, for example by those cyclic alkyl groups mentioned above.

As the halogenating agent, use is made of a halogen such as chlorine, bromine and iodine, halogen halides such as iodine chloride, iodine bromide and bromine chloride, hypohalogenous acids such as hypochlorous acid, hypobromous acid and hypoiodous acid, salts of hypohalogenous acids with metals such as sodium, potassium, calcium, barium and copper (cuprous and cupric), hypohalogenous acid esters such as methyl, ethyl, tert-butyl and 2,4,6-tribromophenyl esters of hypohalogenous acids, N-halogenosuccinimides such as N-chlorosuccinimide, N-bromosuccinimide and N-iodosuccinimide, metal halides such as titanium tetrachloride, cupric bromide and potassium bromide, N,N-dibromobenzenesulfonamide, N-chloroacetamide, N-bromoacetamide, N-bromopropionamide, trichloroisocyanuric acid, N-chlorourea, methyl N,N-dichlorocarbamate, ethyl N-chlorocarbamate, iodobenzenedichloride, bromotrinitromethane, etc. These reagents may be employed together with oxidizing agents such as oxygen and hydrogen peroxide, acids such as p-toluenesulfonic acid, formic acid, acetic acid, hydrochloric acid, sulfuric acid and boron trifluoride, heavy metal salts of organic carboxylic acids such as silver acetate, silver n-butyrate, silver benzoate and thallium acetate, heavy metal oxides such as silver oxide and mercury oxide, metal carbonates such as silver carbonate and potassium carbonate, alkali metal halides such as sodium iodide, potassium iodide, lithium bromide and lithium chloride, bases such as pyridine, etc.

The reaction is normally carried out in solvents such as water, lower alcohols (e.g. methyl alcohol, ethyl alcohol, n-propyl alcohol, isopropyl alcohol, n-butyl alcohol, isobutyl alcohol, sec-butyl alcohol and tert-butyl alcohol etc.), N,N-dimethylformamide, dimethylsulfoxide, sulfolane, dioxane, tetrahydrofuran, acetonitrile, acetone, chloroform, dichloromethane, carbon tetrachloride, benzene, and acetic acid, solely or as a mixed solvent. The reaction temperature is not particularly limited, and the reaction is carried out normally at 0° to 70° C. Depending on the type of halogenating agents, the reaction may be conducted, by cooling or by heating, in the range of from −80° C. to the refluxing temperature of the solvent. The reaction time varies depending upon the reaction temperature, and is normally in the range of 30 minutes to 24 hours.

The thus obtained compound [I] wherein X is a hydroxyl group and Y is a halogen can be led to valiolamine by dehalogenation and hydrolysis, and, if necessary removing the protective group. In dehalogenation, use is advantageously made of a wide variety of metal hydride complex reducing agents, particularly boron hydride complex such as sodium borohydride, potassium borohydride, lithium borohydride, sodium trimethoxyborohydride, lithium triethylborohydride, and sodium borocyanohydride.

As a reaction solvent, for example, use can be made of water, alcohols such as methanol, ethanol, propanol and butanol, N,N-dimethylformamide, N-methylacetamide, dimethylsulfoxide, glymes such as methyl cellosolve, dimethyl cellosolve and diethylene glycol dimethyl ether, dioxane, tetrahydrofuran, acetonitrile, or mixed solvents thereof or mixtures of these polar solvents with non-polar solvents such as ethyl acetate and benzene.

The reaction conditions vary with the type of reducing agents, and as to the reaction temperature, the reaction is conducted normally at room temperature, under ice-cooling as the case may be, or by heating up to the refluxing temperature of the solvent when occasion demands. The reaction time also varies depending upon the reaction temperature as well as the type of reducing agents, and the objective can be achieved by conducting the reaction normally for a period of time in the range of several minutes to 24 hours.

As the procedure of dehalogenation, use can be made of the catalytic reduction procedure as well. that is to say, the procedure can be conducted into practice by shaking or stirring a starting material in an appropriate solvent under a stream of hydrogen in the presence of a catalyst for catalytic reduction. As the catalyst for catalytic reduction, for example, use is made of palladium carbon, palladium black, Raney nickel, platinum black, platinum dioxide, etc. As the reaction solvent, for example, use is made of water, alcohols such as methanol and ethanol, dioxane, tetrahydrofuran, dimethylformamide or mixed solvents thereof. The reaction is conducted normally at ordinary temperature and at atmospheric pressure, but also may be carried out under pressure or under heating. The reaction time is normally in the range of 2 to 18 hours.

In addition, dehalogenation by the use of an organic tin hydride may be carried out. That is to say, the objective can be achieved by suspending or dissolving a starting material in an organic solvent such as benzene, toluene, xylene, ethyl ether, dioxane and diethylene glycol monoethyl ether etc., and adding for reaction an organic tin hydride such as (n-$C_4H_9$)$_3$SnH, (n-$C_4H_9$)$_2$SnH$_2$, (n-$C_3H_7$)$_3$SnH, ($C_2H_5$)$_3$SnH, ($C_6H_5$)$_3$SnH and ($C_6H_5$)$_2$SnH$_2$ etc., and an initiator for radical reaction (e.g., azo compounds such as $\alpha,\alpha'$-azobisisobutyronitrile, peroxides such as benzoyl peroxide, others such as triphenylboric acid, etc.), preferably $\alpha,\alpha'$-azobisisobutyronitrile.

Besides, use can be made of the procedure which comprises conducting dehalogenation with the use of metal complexes of aluminium hydride such as lithium aluminium hydride, sodium aluminium hydride, sodium triethoxyaluminium hydride, sodium bis(2-methoxyethoxy)aluminium hydride and sodium diethylaluminium hydride, the procedure consisting of a reaction with sodium or lithium or liquid ammonia, the procedure of conducting dehalogenation with zinc and hydrochloric acid or acetic acid, the procedure of carrying out dehalogenation by an electrolytic reduction reaction, etc. The reaction mixture as obtained by the above procedure may be subjected to hydrolysis without prurification or after being partly purified. The hydrolysis of the cyclic carbamate bond (—O—CO—NH—) in the compounds [I] is conducted normally in an aqueous solution or an appropriate solvent such as organic solvents exemplified by methanol, ethanol, propanol, acetone, dioxane and tetrahydrofuran or mixed solution thereof with water in the presence of inorganic base such as alkali metal hydroxide alkaline earth-metal hydroxide (e.g. sodium hydroxide, potassium hydroxide, barium hydroxide and sodium methoxide etc.) or in the presence of inorganic acids such as hydrochloric acid and sulfuric acid etc. The reaction temperature is normally from room temperature to the refluxing temperature of the solvent, while the reaction time varies depending upon the reaction temperaturs and is normally in the neighborhood of 5 to 24 hours.

Dehalogenation may be conducted after hydrolyzing the cyclic carbamate bond (—O—CO—NH—) in the compound, or the hydrolysis and dehalogenation may be carried out at the same time.

The compound [I] wherein X is a halogen and Y is hydrogen may be acyloxylated to give a compound of the formula

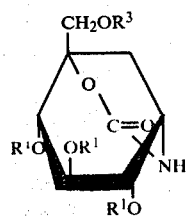

[III]

wherein $R^1$ and $R^3$ are as defined above.

In the acyloxylation reaction, use is normally made of metal salts of carboxylic acids. As such metal salts of carboxylic acids, use is made of salts of lower alkyl carboxylic acids such as formic acid, acetic acid, propionic acid and butyric acid and aromatic carboxylic acids such as benzoic acid with metals such as sodium, potassium and silver. As the suitable solvents, use is made of organic solvents such as dimethylformamide, dimethylacetamide, 2-methoxyethanol, dioxane and tetrahydrofuran, solely or as mixed solvent, or the mixed solvents of these solvents with water. The reaction is preferably carried out by heating to about 50° to 150° C. and the reaction time varies with the reaction temperature and is normally in the range of 1 to 24 hours.

The reaction may be normally conducted in a suitable solvent. In cases in which a water-containing solvent is employed as solvent, the hydrolysis reaction in some instances takes place simultaneously with acyloxylation to form hydroxymethyl derivatives or a reaction of eliminating or replacing the hydroxyl-protecting group may take place. Such reactions also fall into the scope of the present invention.

Valiolamine can be obtained by subjecting to a hydrolysis reaction the compounds of the formulas [I] wherein Y is hydrogen. The hydrolysis reaction of the cyclic carbamate bond (—O—CO—NH—) in the compounds, and the hydrolysis reaction to the —CH$_2$OH group of the —CH$_2$X group (X is a halogen or an acyloxy group) in the compounds are carried out in the presence of inorganic base such as sodium hydroxide, potassium hydroxide, barium hydroxide and calcium hydroxide, or in the presence of acids such as hydrochloric acid and sulfuric acid. As the reaction solvent, use is normally made of water, and in addition, lower alcohols such as methanol, ethanol, propanol and butanol, and organic solvents such as dioxane, tetrahydrofuran, acetone, dimethylformamide and dimethylsulfoxide, solely or as mixed solvent, or the mixed solvents thereof with water. The reaction temperature is normally in the range of room temperature to 150° C., and the reaction time varies with the reaction temperature as well and is normally in the range of 1 to 24 hours. The elimination reaction of the acyl group of $R^3$ in the compounds of the formula [III] normally takes place simultaneously with the hydrolysis reaction of the cyclic carbamate bond (—O—CO—NH—) under the above-mentioned hydrolysis conditions. Yet, when only the elimination reaction of the acyl group of $R^3$ is carried out separately, such reaction can be conducted under milder hydrolysis conditions, for example by employing weak bases such as ammonia. In the step of converting the compounds of the formula [I] wherein Y is hydrogen;

into valiolamine, the conversion reaction of the —CH$_2$X group to the —CH$_2$OH$_3$group, or the hydrolysis reaction of the acyl group of $R^3$, the hydrolysis reaction of the cyclic carbamate bond (—O—CO—NH—) and the reaction of removal of the hydroxyl protective group of $R^1$ may all be carried out simultaneously or may each be conducted separately and the order of these reaction may be optionally reversed.

Although it is not always necessary to introduce the hydroxyl protective group of $R^1$, such introduction in some instances are advantageous, for example, for the purpose of enhacing the solubilities of compounds in reaction solvent or of avoiding undesirable side reactions. These protective groups, after the reaction, may be removed by the known procedures which are suitable for their respective protective group.

In a series of steps for deriving valiolamine from a compound of the formula [II], it is not always necessary to isolate intermediates in the respective steps, and the reaction mixture may be employed in the reaction of the subsequent step as such or after being purified to some extent.

Valiolamine has an inhibitory activity against α-glucoside hydrolase. Namely, the valiolamine suppresses the metabolism of carbohydrates in man and other animals, and exhibits the blood-sugar elevation suppressing function, and is found to be stable crystals or powder and almost free from toxicity ($LD_{50}$ in rats, not lower than 500 mg/kg) and is useful for hyperglycemic symptoms and various disorders caused by hyperglycemia such as obesity, adiposity, hyperlipemia (arteriosclerosis), diabetes, and prediabetes as well as prophylaxis of diseases attributable to sugar metabolism by microorganisms in oral cavity such as dental carries. Valiolamine or a salt thereof is used solely or as mixtures with non-toxic carriers, and may be utilized with liquid or solid foods such as coffee, beverages, fruit juice, beer, milk, jam and sweet bean jam (strained or mashed bean paste boiled down with sugar) etc., seasoning agents, or the principal and subsidiary foods, etc. Foods prepared by adding valiolamine or a salt thereof is useful as a therapeutic diet for patients affected with metabolic abnormality and as a prephylactic diet for healthy persons as well. In addition, valiolamine is of use as an additive for livestock feed which helps to obtain low-fat, high-quality animal flesh for food. Therefore, valiolamine is of value as drugs, food additives and livestock feed additives solely or with an appropriate carrier. Valiolamine is administered orally or parenterally, preferably orally. It can be used directly or in the form of a food additive, or can be administered before or after meals. It can also be used in combination with sweetening, preservatives, dispersing agents and coloring agents.

Specifically, a postprandial blood glucose rise can be suppressed, for example, by taking the preparations containing about 20 to 500 mg of valiolamine after each meal. In addition, valiolamine in the range of 0.01 to 1% relative to the carbohydrate content of food, for example, may be added to various foods.

In the case of blending into livestock feed, the addition ratio of 0.001 to 1% relative to the carbohydrate content of feed is desirable.

The exomethylene derivative (6), that is the compound [II] wherein —A—B— is

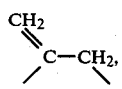

can be produced for example by the procedure as shown in FIG. 1, using validamine [The Journal of Antibiotics, vol. 24, pp 59 to 63 (1971)] as a starting material.

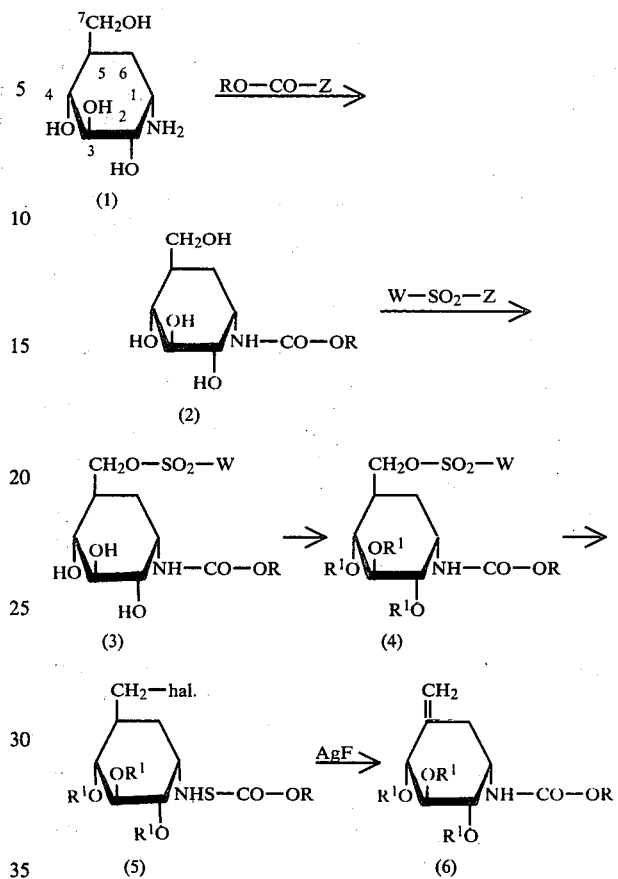

The position number for each of the carbon atoms is assigned as shown in validamine of the formula (1) of FIG. 1 when "Validamine" is employed in the nomenclature of the present compounds.

The compound (2) in FIG. 1 is obtained by reacting validamine (1) with a carbonylating agent of the formula RO—CO—Z. In the carbonylating agent, Z is a halogen such as chlorine and bromine, or a residue of active esters which are prepared by coupling N-hydroxysuccinimide, N-hydroxyphthalimide, N-hydroxy-5-norbornene-2,3-dicarboxyimide, 2-hydroxyimino-2-phenylacetonitrile, N-hydroxypiperidine, 3-hydroxypyridine, p-nitrophenol, 2,4-dinitrophenol, pentachlorophenol, 2,4,5-trichlorophenol, imidazole, 1-hydroxybenzotriazole, 4,6-dimethyl-2-mercaptopyridine, 4,6-dimethylaminopyridine, or 4,6-diethylaminopyridine, etc., with said carboxylic acid; Z may also be a carbonic ester residue as is the case with di-tert-butyl carbonate, diethyl carbonate, diphenyl carbonate, etc.

The reaction of the amino group of validamine with the above carbonylating agent can be carried out in water, or other suitable solvent such as organic solvents exemplified by acetone, dioxane, tetrahydrofuran, methanol, dimethylformamide, chloroform and dichloromethane, solely, or as mixed solvent or mixed solvent thereof with water. This reaction is carried out in the presence of an inorganic base such as sodium hydrogen carbonate, sodium carbonate, sodium hydroxide, potassium hydroxide, lithium hydroxide, barium hydroxide and magnesium oxide, or an organic base such as tertiary amines exemplified by triethylamine, tributylamine, N-methylmorpholine and pyridine. The reaction is desirably conducted at the pH of the reaction mixture in the range of 7 to 12. The reaction temperature is normally in the neighborhood of −10° to 60° C., and the reaction time varies with the reaction temperature and is normally in the range of 30 minutes to 24 hours.

The 7-deoxy-7-halogenovalidamine derivatives of the formula (5) can be synthesized from compounds of the formula (2) by employing the procedure of converting the primary hydroxyl group into halogenomethyl group as generally used in carbohydrate chemistry [refer to "Deoxy Sugars, Advances in Chemistry", series 74, pp. 159 to 201 (1968), published by American Chemical Society; "Methods in Carbohydrate Chemistry", vol. 6, pp. 179 to 207 (1972); "Advances in Carbohydrate Chemistry and Biochemistry", vol.28, pp. 225 to 306 (1973) and vol.33, pp. 72 to 86 (1976), and others], etc. More specifically, the compounds of the formula (5) can be synthesized as well by the procedure that passes via 7-O-sulfonyl derivatives of the formulas (3) and (4) as shown in FIG. 1. That is to say, such compounds can be obtained by reacting a compound of the formula (2) with a sulfonylating agent of the general formula W—SO$_2$—Z (where W—SO$_2$— is an alkylsulfonyl group such as mesyl and ethanesulfonyl, an aralkylsulfonyl group such as benzylsulfonyl, or an arylsulfonyl group such as tosyl, mesythylenesulfonyl, p-bromobenzenesulfonyl and 2-naphthalenesulfonyl; Z is a halogen such as chlorine, bromine and iodine, or an active ester residue such as imidazole group). The reaction is normally carried out in a suitable solvent such as dimethylformamide, pyridine, acetone, dioxane, tetrahydrofuran, chloroform, dichloromethane, benzene and toluene, solely or as mixed solvent, in the presence of an organic base such as pyridine, triethylamine and sodium methylate, or an inorganic base such as sodium hydride. The reaction temperature is preferably −10° to 50° C., and the reaction time varies with the reaction temperature and is normally in the range of 1 to 50 hours. The hydroxyl groups in 2, 3 and 4-positions of the validamine derivatives may be protected with protective groups of R$^1$ as described above, if necessary.

The conversion into a halogen of the sulfonyloxy group in the compounds of the formula (3) or (4) is conducted for example by dissolving or suspending a compound of the formula (3) or (4) in a suitable solvent such as dimethylformamide, dimethylsulfoxide, hexamethylphosphoramide, acetone, benzene, toluene and acetic anhydride, solely or as mixed solvent, and adding to the resulting solution or suspension salts of hydrohalogenic acid such as halogen hydroiodic acid, hydrobromic acid, hydrochloric acid etc., with alkali or alkaline earth metals such as sodium, potassium, lithium and magnesium, followed by the reaction at about 50° to 150° C. The reaction time varies with the reaction temperature and is in the range of 30 minutes to 36 hours.

As the procedure of producing the exomethylene derivatives (6) from the halogenomethyl derivatives (5), the method known in carbohydrate chemistry such as the procedure of producing 5-enopyranose having exomethylene group from 6-deoxy-6-halogenohexose [e.g., the procedures described in "Deoxy Sugars, Advances in Chemistry" series 74, pp. 120 to 140 (1968), published by American Chemical Society; "Methods in Carbohydrate Chemistry", vol. 2, pp. 415 to 418 (1963) and vol. 8, pp. 201 to 205, pp. 301 to 304 (1980), and others] can be applied.

More specifically, the exomethylene derivatives [II] can be produced by reacting a halogenomethyl derivative (5) with a dehalogenating agent such as silver fluoride, at 10° to 40° C. for a period of time in the range of 1 to 24 hours, in a suitable solvent in the presence of a base such as pyridine.

The compounds (6), wherein R$^1$ is hydrogen, can be obtained for example by eliminating the hydroxyl protective group of a compound where R$^1$ is a hydroxyl protective group under such reaction conditions as may allow the elimination without splitting the urethane bond (—NH—C—O—). In cases in which R$^1$ is an acyl type protective group such as an acetyl group, for example, the objective can be achieved by effecting hydrolysis with use of inorganic bases such as sodium hydroxide, potassium hydroxide, barium hydroxide, ammonia, sodium methylate and sodium ethylate, organic bases such as ethylamine, diethylamine, triethylamine and pyridine, and bases such as basic ion exchange resins exemplified by Amberlite IRA-400 (produced by Rohm & Haas Co.) and Dowex 1×8 (produced by Dow Chemical Co.), preferably ammonia. As the reaction solvent, use is made of water, lower alcohols such as methanol, ethanol, propanol and butanol, dioxane, tetrahydrofuran, acetone, dimethylformamide, dimethylsulfoxide, diethyl ether, dichloromethane, chloroform, toluene, etc., solely or as a mixed solvent. The reaction is carried out normally at room temperature, by by cooling to temperatures in the neighborhood of −20° C. or by heating to temperatures in the neighborhood of 50° to 60° C., according to the type of bases used. The reaction time varies with the reaction temperature and is normally in the range of 30 minutes to 5 days.

The starting compound [II] wherein —A—B— is

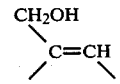

is obtained by reacting valienamine, for example, with a carbonylating agent of the formula RO—CO—Z wherein R and Z are as defined above.

The reaction between the amino group of valienamine and the above-mentioned carbonylating agent can be carried out in water, or other appropriate solvents such as organic solvents exemplified by acetone, dioxane, tetrahydrofuran, methanol, dimethylformamide, chloroform and dichloromethane etc., solely, or as mixed solvent or mixed solvent thereof with water. This reaction is desirably conducted in the presence of inorganic bases exemplified by sodium hydrogen carbonate, sodium carbonate, sodium hydroxide, potassium hydroxide, lithium hydroxide, barium hydroxide and magnesium oxide, and organic bases such as tert-amines exemplified by triethylamine, tributylamine, N-methylmorpholine and pyridine, with the pH of the reaction solution maintained in the range of 7 to 12. The reaction is carried out normally at temperature in the range of −10° to 60° C., while the reaction time is normally 30 minutes to 24 hours.

The compound [I] and valiolamine etc., as obtained by the above procedure can be isolated and purified by the means known per se such as filtration, centrifugation, concentration, concentration under reduced pressure, drying, lyophilization, adsorption, desorption, procedures utilizing the difference in solubility in a variety of solvents (e.g. solvent extraction, precipitation, crystallization, recrystallization, etc.), chromatography (e.g., chromatography employing ion exchange resins, activated carbon, high-porous polymers, Sephadex, Sephadex ion exchange materials, cellulose, ion exchange cellulose, silica gel, alumina, etc.), and others.

Below described are Test example, Reference examples and Examples to illustrate in detail the content of the present invention.

In the following Reference Examples and Examples, the eluate in column chromatography was monitored by thin layer chromatography (TLC) with pre-coated silica gel plate (Kieselgel 60 F$_{254}$, Merck, W. Germany). The TLC was developed with n-propyl alcohol-acetic acid-water (4:1:1), and detection was effected by UV irradiation or with iodine vapor, unless otherwise specified.

TEST EXAMPLE

The method of assaying the glucosidase inhibitory activity.

The inhibitory activities of valiolamine against α-glucosidase (yeast, type I, produced by Sigma Chemical Co., U.S.A.) as well as maltase and saccharase prepared from porcine intestinal mucosa (prepared in accordance with the procedure as described by B. Borgström and A. Dahlqvist in Acta Chem. Scand.; 12, 1997–2006, (1958)), when maltose and sucrose are used as a substrate, are determined by adding to 0.25 ml of a solution of an enzyme prepared by diluting suitably with 0.02 M phosphate buffer (pH 6.8) 0.5 ml of a solution of valiolamine to be tested in the same buffer and 0.25 ml of 0.05 M maltose or 0.05 M sucrose as the substrate in the same buffer allowing the mixture to react at 37° C. for 10 minutes, then adding 3 ml of Glucose B-Test Reagent (a glucose oxidase reagent for measurement of glucose, produced by Wako Pure Chemical Co., Japan), further warming the mixture at 37° C. for 20 minutes and measuring the absorbance of the reaction solution at 505 nm.

The inhibitory activities against α-glucosidase (yeast, type I, produced by Sigman Chemical Co.) and glucoamylase (Rhizopus mold, produced by Sigma Chemical Co.) when p-nitrophenyl α-D-glucopyranoside is used as a substrate, are determined by adding to 0.25 ml of 0.02 M phosphate buffer (pH 6.8) containing 0.005 mg/ml of α-glucosidase 0.5 ml of a solution of valiolamine in the same buffer and 0.25 ml of a solution of 0.01 M p-nitrophenyl α-D-glucopyranoside in the same buffer, allowing the reaction to proceed at 37° C. for 15 minutes, then adding 3 ml of 0.1 M aqueous sodium carbonate solution to terminate the reaction, and measuring the absorbance of the reaction solution at 400 nm. The 50% inhibition concentration is calculated from the inhibition rates (%) which are determined with inhibitory substance samples of three to five different concentrations.

Table 1 shows the concentration of 50% inhibition against α-glucosidase (IC$_{50}$) of valiolamine.

TABLE 1

| Enzyme (source) | Substrate | IC$_{50}$ (M) |
| --- | --- | --- |
| α-glucosidase (yeast) | 0.01 M p-nitrophenyl α-D-glucopyranoside | $1.1 \times 10^{-3}$ |
| α-glucosidase (yeast) | 0.05 M maltose | $1.9 \times 10^{-4}$ |
| maltase (porcine, intestinal mucosa) | 0.05 M maltose | $2.2 \times 10^{-6}$ |
| saccharase (porcine, intestinal mucosa) | 0.05 M sucrose | $4.9 \times 10^{-8}$ |
| glucoamylase (rhizopus mold) | 0.01 M p-nitrophenyl α-D-glucopyranoside | $6.0 \times 10^{-4}$ |

REFERENCE EXAMPLE 1

N-Benzyloxycarbonylvalienamine

In 300 ml of water is dissolved 15 g of valienamine, and after the addition of 100 ml of ethyl acetate, 25 ml of benzyloxycarbonyl chloride and 12 g of sodium hydrogencarbonate are added at once to the solution under ice-cooling, followed by stirring at room temperature for 3 hours. The reaction mixture is adjusted to pH 6, and then, the water layer is separated and washed with ethyl acetate. The water layer is concentrated under reduced pressure to about 150 ml, and the concentrate is allowed to stand overnight in a refrigerator to give crystals of N-benzyloxycarbonylvalienamine. Yield of 16.4 g.

The mother liquor is chromatographed on a column of MCI Gel CHP 20P (produced by Mitsubishi Chemical Ind., Ltd., Japan, 350 ml), and after the column is washed with water, elution is performed with a water-80% aqueous methanol gradient. The eluate containing the objective compound is concentrated under reduced pressure and then lyophilized to give white powder of N-benzyloxycarbonylvalienamine. Yield of 3.5 g.

Elemental analysis, for C$_{15}$H$_{19}$NO$_6$: Calcd. (%): C, 58.24; H, 6.19; N, 4.53. Found (%): C, 58.38; H, 6.24; N, 4.54.

$[\alpha]_D^{26} + 125.4°$ (c=1, H$_2$O).

REFERENCE EXAMPLE 2

N-Ethoxycarbonylvalienamine

A 25 g portion of valienamine is dissolved in a mixed solution of 360 ml of water and 180 ml of dioxane, and the solution is cooled to 0° to 5° C. 25 g of ethyl chlorocarbonate is added to the solution, which is stirred at the same temperature for 1 hour, while adjusting it to pH 7 by adding dropwise a saturated aqueous solution of sodium hydrogen carbonate. The reaction mixture is adjusted to pH 5.5 by adding 2 N hydrochloric acid, and subsequently concentrated under reduced pressure. The residue is chromatographed on a column of Amberlite CG-50 (H$^+$ type, produced by Rohm & Haas Co., U.S.A., 1.5 l), and elution is effected with water. The eluate containing the objective compound is concentrated under reduced pressure and then lyophilized to give white powder of N-ethoxycarbonylvalienamine. Yield of 26.2 g.

Elemental analysis, for C$_{10}$H$_{17}$NO$_6$: Calcd. (%): C, 48.58; H, 6.93; N, 5.67. Found (%): C, 48.30; H, 6.87; N, 5.37.

$[\alpha]_D^{26} + 123.9°$ (c=1, H$_2$O).

REFERENCE EXAMPLE 3

N-Benzyloxycarbonylvalidamine

In 250 ml of water is dissolved 21 g of validamine, and 125 ml of dioxane is added to the solution, to which 22.5 ml of benzyloxycarbonyl chloride is added under ice-cooling (0° to 5° C.). The solution is stirred at 0° to 5° C. for 1 hour and then at room temperature for 1 hour, while it is adjusted to pH 7 to 7.5 with a saturated aqueous solution of sodium hydrogen carbonate. The reaction mixture is adjusted to pH 5.5 by adding dropwise 2 N hydrochloric acid, and the organic solvent is distilled off under reduced pressure. About 250 ml of water is added to the concentrate, and the mixture is washed with ethyl acetate, followed by concentrating the water layer under reduced pressure. The residue is chromatographed on a column of Amberlite CG-50 (H+ type, 800 ml, produced by Rohm & Haas Co.), and elution is performed with water. The eluate containing the objective compound is concentrated under reduced pressure and lyophilized to give 31.8 g of N-benzyloxycarbonylvalidamine.

Elemental analysis, for $C_{15}H_{21}NO_6$: Calcd. (%): C, 57.86; H, 6.80; N, 4.50. Found (%): C, 57.50; H, 6.81; N, 4.45.

$[\alpha]_D^{24} + 55.5°$ (c=1, $H_2O$).

REFERENCE EXAMPLE 4

N-Benzyloxycarbonyl-7-O-p-toluenesulfonylvalidamine

A 3.8 g portion of p-toluenesolfonyl chloride is added to a solution of 6.0 g of N-benzyloxycarbonylvalidamine in 60 ml of pyridine under cooling with ice water, and the solution is stirred at room temperature for 15 hours. The reaction solution is concentrated under reduced pressure, and the residue is added to a mixture consisting of ethyl acetate and water and partitioned between them, followed by separating the ethyl acetate layer. The water layer is extracted with ethyl acetate. The ethyl acetate layers are combined, washed first with 1 N hydrochloric acid then saturated aqueous sodium hydrogen carbonate, dried over sodium sulfate, and concentrated under reduced pressure. The residue is chromatrographed on a column of silica gel (400 ml), and elution is performed with ethyl acetate. The eluate containing the objective compound is concentrated under reduced pressure, and 500 ml of a solution consisting of a mixture of ethyl ether and a peroleum ether (1:3) is added to the residue. The mixture is allowed to stand overnight in a refrigerator to give 5.1 g of N-benzyloxycarbonyl-7-O-p-toluenesulfonylvalidamine.

Elemental analysis, for $C_{22}H_{27}NO_8S$: Calcd. (%): C, 56.76; H, 5.85; N, 3.01; S, 6.89. Found (%): C, 57.08; H, 5.89; N, 3.38; S, 6.98.

NMR (DMSO-$d_6$)δ: 2.41(3H,s), 5.00(2H,s), 7.37(5H,s), 7.45(2H,d,J=8 Hz), 7.76(2H,d,J=8 Hz).

REFERENCE EXAMPLE 5

2,3,4-Tri-O-acetyl-N-benzyloxycarbonyl-7-O-p-toluenesulfonylvalidamine

In 200 ml of pyridine is dissolved 21 g of N-benzyloxycarbonyl-7-O-p-toluenesulfonylvalidamine, and 100 ml. of acetic anhydride is added to the solution, followed by stirring at room temperature for 16 hours. The reaction solution is concentrated under reduced pressure, and the residue is dissolved in ethyl acetate. The solution is washed with 2 N hydrochloric acid and a saturated aqueous solution of sodium hydrogen carbonate, dried over sodium sulfate, and concentrated under reduced pressure. About 1 l of ethyl ether and petroleum ether (1:4) is added to the residue, and the mixture is allowed to stand overnight in a refrigerator to give 26.2 g of crystals of 2,3,4-tri-O-acetyl-N-benzyloxycarbonyl-7-O-p-toluenesulfonylvalidamine.

Elemental analysis, for $C_{28}H_{33}NO_{11}S$: Calcd. (%): C, 56.84; H, 5.62; N, 2.37; S, 5.42. Found (%): C, 56.69; H, 5.72; N, 2.39; S, 5.13.

mp 80°-81° C.

$[\alpha]_D^{24} + 55.5°$ (c=1, $CH_3OH$).

NMR (CDCl$_3$)δ: 1.92(6H,s), 1.95(3H,s), 2.44(3H,s), 3.93(2H,d,J=6 Hz), 4.1-4.4(1H,m), 4.7-5.5(3H,m), 5.09(2H,s), 7.35(2H,d,J=8 Hz), 7.36(5H,s), 7.76(2H,d,J=8 Hz).

REFERENCE EXAMPLE 6

2,3,4-Tri-O-acetyl-N-benzyloxycarbonyl-7-deoxy-7-iodovalidamine

In 60 ml of acetic anhydride is dissolved 20 g of 2,3,4-tri-O-acetyl-N-benzyloxycarbonyl-7-O-p-toluenesulfonylvalidamine, and 6 g of sodium iodide is added to the solution and the mixture is stirred for 30 minutes under heating at 120° to 130° C. After the reaction mixture is cooled to room temperature, acetone is added, and the resulting crystals are filtered and washed with acetone. The filtrate and washings are combined and concentrated under reduced pressure. The residue is added to a mixed solvent of ethyl ether and water. Then, the ethyl ether layer is separated, washed with a mixture consisting of a saturated aqueous solution of sodium hydrogen carbonate and a 5% aqueous solution of sodium thiosulfate (5:1), dried over magnesium sulfate, and concentrated under reduced pressure. The residue is chromatographed on a column of silica gel (400 ml), and elution is performed with toluene-ethyl acetate (4:1). The eluate containing the objective compound is concentrated under reduced pressure, and the residue is dissolved in a small amount of ethyl ether under heating. Petroleum ether is added to the solution, followed by ice-cooling to give 16.9 g of crystals of 2,3,4-tri-O-acetyl-N-benzyloxycarbonyl-7-deoxy-7-iodovalidamine.

Elemental analysis, for $C_{21}H_{26}NO_8I$: Cacld. (%): C, 46.08; H, 4.79; N, 2.56. Found (%): C, 46.57; H, 4.77; N, 2.51.

mp 85°-86° C.

$[\alpha]_D^{24} + 49.5°$ (c=1, $CH_3OH$).

NMR (CDCl$_3$)δ: 1.92(3H,s), 1.97(3H,s), 2.00(3H,s), 3.01(1H,dd,J=6 Hz, 10 Hz), 3.21(1H,dd,J=3 Hz, 10 Hz), 4.15-4.4(1H,m), 4.7-5.4(3H,m), 5.09(2H,s), 7.37(5H,s).

REFERENCE EXAMPLE 7

N-Benzyloxycarbonyl-tri-O-acetyl-D-(1,3,6/2)-6-amino-4-methylene-1,2,3-cyclohexanetriol In 90 ml of pyridine is dissolved 15 g of 2,3,4-tri-O-acetyl-N-benzyloxycarbonyl-7-deoxy-7-iodovalidamine, and 15 g of silver fluoride is added to the solution, followed by stirring at 20° to 25° C. for 3.5 hours. The reaction mixture is added to 1.5 l of ethyl ether, and the mixture is stirred. The resulting precipitate is filtered, and washed with ethyl ether. The filtrate and washings are combined, washed with a mixed solution (5:1) of a saturated aqueous solution of sodium hydrogen carbonate and a 5% aqueous solution of sodium thiosulfate, dried over magnesium sulfate, and concentrated under reduced pressure. The residue is chromatographed on a column of silica gel (550 ml), and elution is performed with toluene-ethyl acetate (3:1). The eluate containing the objective compound is combined, and concentrated to dryness under reduced pressure, followed by drying overnight in a desiccator to give 11.6 g of N-benzyloxycarbonyl-tri-O-acetyl-D-(1,3,6/2)-6-amino-4-methylene-1,2,3-cyclohexanetriol.

Elemental analysis, for $C_{21}H_{25}NO_8$: Calcd. (%): C, 60.13; H, 6.01; N, 3.34. Found (%): C, 60,31; N, 6.13; N, 3.09.

$[\alpha]_D^{24}+25.0°$ (c=1, $CH_3OH$).

NMR ($CDCl_3$)δ: 1.91(3H,s), 2.00(3H,s), 2.09(3H,s), 2.47(2H,d,J=4 Hz), 4.25–4.55(1H,m), 4.7–5.5(3H,m), 5.08(2H,s), 7.23(1H,d,J=6.5 Hz), 7.37(5H,s).

REFERENCE EXAMPLE 8

N-Benzyloxycarbonyl-D-(1,3,6/2)-6-amino-4-methylene-1,2,3-cyclohexanetriol

In 50 ml of ethanol is dissolved 6.0 g of N-benzyloxycarbonyl-tri-O-acetyl-D-(1,3,6/2)-6-amino-4-methylene-1,2,3-cyclohexanetriol, and 50 ml of 10% aqueous ammonia is added to the solution, followed by stirring at room temperature for 4 hours and leaving on standing at room temperature for 4 days. The reaction solution is concentrated under reduced pressure, and 50 ml of 50% aqueous ethanol is added to the residue. The mixture is allowed to stand overnight in a refrigerator to give 3.5 g of crystals of N-benzyloxycarbonyl-D-(1,3,6/2)-6-amino-4-methylene-1,2,3-cyclohexanetriol.

Elemental analysis, for $C_{15}H_{19}NO_5$: Calcd. (%): C, 61.42; H, 6.53; N, 4.78. Found (%): C, 61.14; H, 6.34; N, 4.47.

mp 119°–120° C.

$[\alpha]_D^{23}+36.5°$ (c=1, $CH_3OH$).

EXAMPLE 1

9-Bromo-6,7,8-trihydroxy-1-hydroxymethyl-3-oxo-2-oxa-4-azabicyclo[3.3.1]nonane

A 200 ml portion of an aqueous solution of 9.3 g of benzyloxycarbonylvalienamine and 250 ml of an aqueous solution of 5.3 g of bromine are simultaneously added dropwise to 100 ml of water cooled to 5° to 10° C. over a period of about 1 hour, while maintaining the temperature of the reaction solution at 5° to 10° C. The reaction mixture is further stirred at the same temperature for 1.5 hour, then adjusted to pH 6 with a saturated aqueous solution of sodium hydrogen carbonate, and washed with ethyl acetate. The water layer is concentrated under reduced pressure, and the residue is chromatographed on a column of MCI Gel CHP 20P (produced by Mitsubishi Chemical Ind., Ltd., Japan, 600 ml), followed by elution with water. The eluate containing the objective compound is concentrated to about 50 ml, and the concentrate is allowed to stand in a refrigerator to give crystals of 9-bromo-6,7,8-trihydroxy-1-hydroxymethyl-3-oxo-2-oxa-4-azabicyclo[3.3.1]nonane. Yield of 6.5 g.

Elemental analysis, for $C_8H_{12}NO_6Br.H_2O$: Calcd. (%): C, 30.39; H, 4.46; N, 4.48; Br, 25.28. Found (%): C, 30.30; H, 4.54; N, 4.40; Br, 25.41.

$[\alpha]_D^{24}+41.5°$ (c=1, $H_2O$).

IR $\nu_{max}^{KBr}$ cm$^{-1}$: 1700 (—CO—).

EXAMPLE 2

9-Chloro-6,7,8-trihydroxy-1-hydroxymethyl-3-oxo-2-oxa-4-azabicyclo[3.3.1]nonane

In 300 ml of water is dissolved 2.6 g of chlorine, and the solution is cooled to 0° to 5° C. 250 ml of an aqueous solution of 9.3 g of N-benzyloxycarbonylvalienamine is added dropwise to the solution, which is further stirred at the same temperature for 1.5 hours. The reaction mixture is adjusted to pH 6 by adding a saturated aqueous solution of sodium hydrogen carbonate, and then washed with ethyl acetate. The water layer is concentrated under reduced pressure, and the residue is chromatographed on a column of MCI Gel CHP 20P (produced by Mitsubishi Chemical Ind., Ltd., Japan, 400 ml), followed by elution with water. The eluate containing the objective compound is concentrated under reduced pressure and then lyophilized to give white powder of 9-chloro-6,7,8-trihydroxy-1-hydroxymethyl-3-oxo-2-oxa-4-azabicyclo[3.3.1]nonane.

Elemental analysis, for $C_8H_{12}NO_6Cl.\frac{1}{2}H_2O$: Calcd. (%): C, 36.58; H, 4.99; N, 5.33; Cl, 13.50. Found (%): C, 36.52; H, 5.14; N, 5.25; Cl, 13.87.

$[\alpha]_D^{26}+43.1°$ (c=1, $H_2O$).

IR $\nu_{max}^{KBr}$ cm$^{-1}$: 1700 (—CO—).

EXAMPLE 3

9-Bromo-6,7,8-trihydroxy-1-hydroxymethyl-3-oxo-2-oxa-4-azabicyclo[3.3.1]nonane (a) A 20 ml portion of an aqueous solution of 4.54 g of N-ethoxycarbonylvalienamine and 50 ml of an aqueous solution of 1.76 g of bromine are simultaneously added dropwise to 30 ml of water cooled to 5° to 10° C., while maintaining the temperature of the reaction solution at the same temperature. The reaction solution is further stirred at the same temperature for 1.5 hours, then adjusted to pH 5.4 by adding a saturated aqueous solution of sodium hydrogen carbonate, and concentrated under reduced pressure. The residue is chromatographed on a column of MCI Gel CHP-20P (produced by Mitsubishi Chemical Ind., Ltd., Japan, 250 ml), followed by elution with water. The eluate containing the objective compound is concentrated under reduced pressure and then lyophilized to give white powder of 9-bromo-6,7,8-trihydroxy-1-hydroxymethyl-3-oxo-2-oxa-4-azabicyclo[3.3.1]nonane.

(b) A 50 ml portion of methanol is cooled to 5° to 10° C. To the methanol are simultaneously added dropwise a solution of 9.3 g of N-benzyloxycarbonylvalienamine in 50 ml of methanol and a solution of 5.3 g of bromine in 20 ml of methanol. The reaction solution is further stirred at the same temperature for 1 hour and concentrated under reduced pressure.

400 ml of ethanol-ethyl acetate (1:5) is added to the residue, and the mixture is allowed to stand overnight in a refrigerator to give crude crystals (8.6 g) of 9-bromo-6,7,8-trihydroxy-1-hydroxymethyl-3-oxo-2-oxa-4-azabicyclo[3.3.1]nonane. Recrystallization of said crude crystals from water yields 8.1 g of crystals (prisms).

EXAMPLE 4

6,7,8-Trihydroxy-1-hydroxymethyl-3-oxo-2-oxa-4-azabicyclo[3.3.1]nonane (a) To 50 ml of an aqueous solution of 1.0 g of 9-bromo-6,7,8-trihydroxy-1-hydroxymethyl-3-oxo-2-oxa-4-azabicyclo[3.3.1]nonane is added 20 ml of an aqueous solution of 0.5 g of sodium borohydride at room temperature, and the mixture is stirred for 2 hours. The reaction solution is adjusted to pH 5 by adding acetic acid, and then concentrated under reduced pressure. The residue is chromatographed on a column of activated carbon (180 ml), and the column is washed with water, followed by elution with 50% aqueous methanol. The eluate containing the objective compound is concentrated under reduced pressure, and methanol-ethanol (1:10) is added to the residue, which is allowed to stand in a refrigerator to give crystals of 6,7,8-trihydroxy-1-hydroxymethyl-3-oxo-2-oxa-4-azabicyclo[3.3.1]nonane. Yield of 560 mg.

Elemental analysis, for $C_8H_{13}NO_6$: Calcd. (%): C, 43.83; H, 5.98; N, 6.39. Found (%): C, 43.81; H, 5.95; N, 6.55.

$[\alpha]_D^{24} +36.4°$ (c=1, $H_2O$).

IR $\nu_{max}^{KBr}$ cm$^{-1}$: 1670 (C=O).

NMR ($D_2O$) TMS* (external standard) $\delta$ value: 2.07 (1H,dd,J=2 and 15 Hz), 2.34(1H,dd,J=5 and 15 Hz), 3.45–4.1 (6H).

mp 254°–255° C. (decomp.)

* tetramethylsilane (b) In 100 ml of water is dissolved 2.0 g of 9-bromo-6,7,8-trihydroxy-1-hydroxymethyl-3-oxo-2-oxa-4-azabicyclo[3.3.1]nonane, and 400 mg of palladium black is added to the solution, followed by stirring for 8 hours in a stream of hydrogen at room temperature. The catalyst is filtered off and washed with water. The filtrate and washings are combined, adjusted to pH 6 by adding a saturated aqueous solution of sodium hydrogen carbonate, and concentrated under reduced pressure. The residue is chromatographed on a column of 250 ml of MCI Gel CHP 20P (produced by Mitsubishi Chemical Ind., Ltd., Japan), followed by elution with water. The eluate is chromatographed on a column of activated carbon (250 ml), and the column is washed with water, followed by elution with a water-methanol gradient. The eluate containing the objective compound is concentrated under reduced pressure, and methanol is added to the residue, which is then allowed to stand overnight in a refrigerator to give crystals of 6,7,8-trihydroxy-1-hydroxymethyl-3-oxo-2-oxa-4-azabicyclo[3.3.1]nonane. Yield of 780 mg.

EXAMPLE 5

1L(1S)-(1(OH),2,4,5/1,3)-5-amino-1-hydroxymethyl-1,2,3,4-cyclohexanetetrol (valiolamine)

In 200 ml of water is dissolved 4.0 g of 6,7,8-trihydroxy-1-hydroxymethyl-3-oxo-2-oxa-4-azabicyclo[3.3.1]nonane, and 16 g of barium hydroxide is added to the solution, followed by stirring under heating at 70° to 80° C. for 4 hours. The reaction mixture is cooled to room temperature, and carbon dioxide gas is bubbled into the mixture for 30 minutes. The resulting precipitate of barium carbonate is filtered off. The filtrate is concentrated under reduced pressure, and the concentrate is chromatographed on a column of Amberlite CG-50 ($NH_4^+$ type, produced by Rohm & Haas Co., U.S.A., 250 ml). After the column is washed with water, elution is performed with 0.1 N aqueous ammonia, and the eluate is concentrated under reduced pressure. The residue is chromatographed on a column of Dowex 1×2 (OH$^-$ type, produced by Dow Chemical Co., U.S.A., 1.1 l), and elution is effected with water. The eluate containing the objective compound is concentrated under reduced pressure, and lyophilized to give white powder of 1L(1S)-(1(OH),2,4,5/1,3)-5-amino-1-hydroxymethyl-1,2,3,4-cyclohexanetetrol. Yield of 3.3 g.

Elemental analysis, for $C_7H_{15}NO_5 \cdot H_2O$: Calcd. (%): C, 39.80; H, 8.11; N, 6.63. Found (%): C, 39.94; H, 8.08; N, 6.67.

$[\alpha]_D^{25} +19.6°$ (c=1, $H_2O$).

NMR ($D_2O$) TMS* (external standard) $\delta$ value: 1.80(1H,dd,J=3.8 and 15.5 Hz), 2.07(1H,dd,J=3 and 15.5 Hz), 3.4–3.6(1H), 3.55(1H,d,J=10 Hz), 3.63(2H), 3.72(1H,dd,J=4.2 and 10 Hz), 3.99(1H,t,J=10 Hz).

* tetramethylsilane

EXAMPLE 6

6,7,8-Triacetoxy-1-bromomethyl-3-oxo-2-oxa-4-azabicyclo[3.3.1]nonane

A solution of 4.2 g of N-benzyloxycarbonyl-tri-O-acetyl-D-(1,3,6/2)-6-amino-4-methylene-1,2,3-cyclohexanetriol in 30 ml of methanol is added dropwise to a solution of 1.7 g of bromine in 20 ml of methanol under cooling to 5° to 10° C., and the solution is stirred at 5° to 10° C. for 1.5 hours. The reaction solution is concentrated under reduced pressure, and the residue is dissolved in ethyl acetate. The ethyl acetate solution is washed with 5% aq. sodium thiosulfate, dried over sodium sulfate, and concentrated under reduced pressure. Ethyl ether-petroleum ether (1:1) is added to the residue, and the mixture is allowed to stand overnight in a refrigerator to give 3.3 g of crystals of 6,7,8-triacetoxy-1-bromomethyl-3-oxo-2-oxa-4-azabicyclo[3.3.1]nonane.

Elemental analysis, for $C_{14}H_{18}NO_8Br$: Calcd. (%): C, 41.19; H, 4.44; N, 3.43; Br, 19.58. Found (%): C, 41.17; H, 4.35; N, 3.33; Br, 19.56.

mp 122°–123° C. (decomp.).

$[\alpha]_D^{24} +45.2°$ (c=1, $CH_3OH$).

NMR ($CDCl_3$)$\delta$: 1.97(3H,s,), 2.03(3H,s), 2.24(3H,s), 3.43(2H,s), 3.90(1H,m), 4.9–5.15(1H,m), 5.15–5.45(2H,m), 7.85(1H,d,J=5 Hz).

EXAMPLE 7

6,7,8-Triacetoxy-1-iodomethyl-3-oxo-2-oxa-4-azabicyclo[3.3.1]nonane

A solution of 1.7 g of iodine monochloride in 20 ml of acetonitrile is added dropwise to a solution of 4.2 g of N-benzyloxycarbonyl-tri-O-acetyl-D-(1,3,6/2)-6-amino-4-methylene-1,2,3-cyclohexanetriol in 50 ml of acetonitrile under cooling to 0° to 5° C., and the solution is stirred at the same temperature for 5.5 hours. The reaction solution is concentrated under reduced pressure, and the residue is dissolved in ethyl acetate. The ethyl acetate solution is washed with 5% aqueous sodium thiosulfate, dried over sodium sulfate, and concentrated under reduced pressure. Ethyl ether is added to the residue and the mixture is allowed to stand overnight at room temperature to give 3.7 g of crystals of 6,7,8-triacetoxy-1-iodomethyl-3-oxo-2-oxa-4-azabicyclo[3.3.1]nonane.

Elemental analysis, for $C_{14}H_{18}NO_8I$: Calcd. (%): C, 36.94; H, 3.99; N, 3.08. Found (%): C, 37.07; H, 3.90; N, 3.27.

mp 231°–232° C. (decomp.).

$[\alpha]_D^{24} +35.2°$ (c=1, $CH_3OH$).

NMR (DMSO-$d_6$)δ: 1.97(3H,s), 2.07(3H,s), 2.11(3H,s), 3.33(2H,s), 3.73–3.93(1H,m), 4.8–5.1(1H,m), 5.2–5.45(2H,m), 7.76(1H,d,J=5 Hz).

EXAMPLE 8

1-Bromomethyl-6,7,8-trihydroxy-3-oxo-2-oxa-4-azabicyclo[3.3.1]nonane

In 40 ml of methanol is dissolved 2.9 g of N-benzyloxycarbonyl-D-(1,3,6/2)-6-amino-4-methylene-1,2,3-cyclohexanetriol, and a solution of 1.8 g of bromine in 20 ml of methanol is added dropwise to the solution under cooling at 0° to 5° C., followed by stirring at the same temperature for 1 hour. The reaction solution is concentrated under reduced pressure, and the residue is added to a mixture consisting of ethyl acetate and water. The water layer is separated, washed with ethyl acetate, and concentrated under reduced pressure. The residue is chromatographed on a column of MCI Gel CHP 20P (250 ml), and the column is washed with water, followed by elution with a water-50% aqueous methanol gradient. The eluate is concentrated under reduced pressure to about 20 ml, and the concentrate is allowed to stand overnight in a refrigerator to give 2.4 g of crystals of 1-bromomethyl-6,7,8-trihydroxy-3-oxo-2-oxa-4-azabicyclo[3.3.1]nonane.

Elemental analysis, for $C_8H_{12}NO_5Br$: Calcd. (%): C, 34.06; H, 4.29; N, 4.97; Br, 28.33. Found (%): C, 34.04; H, 4.15; N, 5.00; Br, 28.32.

mp 251°–252° C. (decomp.).

$[\alpha]_D^{23} +6.4°$ (c=1, DMSO).

EXAMPLE 9

6,7,8-Triacetoxy-1-acetoxymethyl-3-oxo-2-oxa-4-azabicyclo[3.3.1]nonane

In 10 ml of dimethylformamide is dissolved 500 mg of 6,7,8-triacetoxy-1-bromomethyl-3-oxo-2-oxa-4-azabicyclo[3.3.1]nonane, and 500 mg of silver acetate is added to the solution, followed by stirring at 120° to 130° C. for 10 hours. The reaction mixture is concentrated under reduced pressure, and the residue is added to a mixture of ethyl acetate and water and partitioned between them. The ethyl acetate layer is separated, washed with 2 N hydrochloric acid and saturated aqueous sodium hydrogen carbonate solution, then dried over sodium sulfate, and concentrated under reduced pressure. Addition of ethyl ether to the residue gives 340 mg of crystals of 6,7,8-triacetoxy-1-acetoxymethyl-3-oxo-2-oxa-4-azabicyclo[3.3.1]nonane.

Elemental analysis, for $C_{16}H_{21}NO_{10}$: Calcd. (%): C, 49.61; H, 5.46; N, 3.62. Found (%): C, 49.68; H, 5.39; N, 3.63.

mp 174°–175° C.

$[\alpha]_D^{24} +61.6°$ (c=1, $CH_3OH$).

NMR (CDCl$_3$)δ: 1.96(3H,s), 2.00(3H,s), 2.07(3H,s), 2.25(3H,s), 3.8–4.0(1H,m), 3.92(1H,d,J=12 Hz), 4.30(1H,d,J=12 Hz), 4.99(1H,dd,J=3 and 10 Hz), 5.28(1H,d,J=10 Hz), 5.38(1H,t,J=10 Hz), 7.95(1H,d,J=5 Hz).

EXAMPLE 10

1L(1S)-(1(OH),2,4,5/1,3)-5-Amino-1-hydroxymethyl-1,2,3,4-cyclohexanetetrol (valiolamine)

In 50 ml of water is suspended 500 mg of 6,7,8-triacetoxy-1-acetoxymethyl-3-oxo-2-oxa-4-azabicyclo[3.3.1]nonane, and 2.5 g of barium hydroxide is added to the suspension, followed by stirring at 90° to 100° C. for 3 hours. Carbon dioxide gas is bubbled into the reaction mixture cooled to room temperature, and the resulting precipitates are filtered off, then washed with water.

The filtrate and washings are chromatographed on a column (180 ml) of Amberlite CG-50 (NH$_4^+$ type, produced by Rohm & Haas Co.), and the column is washed with water, followed by elution with 0.2 N aqueous ammonia. The eluate is concentrated under reduced pressure, and the residue is chromatographed on a column (250 ml) of Dowex 1×2 (OH$^-$ type, produced by Dow Chemical Co.), followed by elution with water. The eluate containing the objective compound is concentrated under reduced pressure, and lyophilized to give 240 mg of valiolamine.

Elemental analysis, for $C_7H_{15}NO_5 \cdot H_2O$: Calcd. (%): C, 39.80; H, 8.11; N, 6.63. Found (%): C, 39.91; H, 8.07; N, 6.68.

NMR (D$_2$O)δ: 1.80(1H,dd,J=3.8 Hz,15.5 Hz), 2.07(1H,dd,J=3 Hz, 15.5 Hz), 3.4–3.6(1H), 3.55(1H,d,J=10 Hz), 3.63(2H), 3.72(1H,dd,J=4.2 Hz,10 Hz), 3.99(1H,t,J=10 Hz).

EXAMPLE 11

1L(1S)-(1(OH),2,4,5/1,3)-5-Amino-1-hydroxymethyl-1,2,3,4-cyclohexanetetrol (valiolamine)

In 50 ml of water is suspended 200 mg of 1-bromomethyl-6,7,8-trihydroxy-3-oxo-2-oxa-4-azabicyclo[3.3.1]nonane, and 1.0 g of barium hydroxide is added to the suspension, followed by stirring for 5 hours under heating at 60° to 70° C. The reaction mixture is cooled to room temperature, and carbon dioxide gas is bubbled into it for about 30 minutes, followed by removing by filtration the resulting precipitates (barium carbonate). The filtrate is chromatographed on a column (150 ml) of Amberlite CG-50 (NH$_4^+$ type, produced by Rohm & Haas Co.), and after the column is washed with water, elution is performed with 0.1 N aqueous ammonia. The eluate containing the objective compound is concentrated under reduced pressure, and the residue is chromatographed on a column (150 ml) of Dowex 1×2 (OH$^-$ type, produced by Dow Chemical Co.), followed by elution with water. The eluate containing the objective compound is concentrated under reduced pressure, and lyophilized to give 104 mg of 1L(1S)-(1(OH),2,4,5/1,3)-5-amino-1-hydroxymethyl-1,2,3,4-cyclohexanenetetrol.

EXAMPLE 12

1-Bromomethyl-6,7,8-trihydroxy-3-oxo-2-oxa-4-azabicyclo[3.3.1]nonane

In 40 ml of methanol is dissolved 2.7 g of N-(tert-butyloxycarbonyol)-D-(1,3,6/2)-6-amino-4-methylene-1,2,3-cyclohexanetriol, and a solution of 1.8 g of bromine in 20 ml of methanol is added dropwise to the solution under cooling at 0° to 5° C., followed by stirring at the same temperature for 1 hour. The reaction solution is concentrated under reduced pressure, and the residue is chromatographed on a column of MCI Gel CHP 20P (250 ml, produced by Mitsubishi Chemical Ind.), followed by elution with a water-50% aqueous methanol gradient. The eluate containing the objective compound is concentrated to about 10 ml, which is then allowed to stand overnight in a refrigerator to give crystals of 1-bromomethyl-6,7,8-trihydroxy-3-oxo-2-oxa-4-azabicyclo[3.3.1]nonane.

Subsequently, the same procedure as in Example 11 is carried out to obtain valiolamine.

EXAMPLE 13

(a) N-Benzyloxycarbonylvalienamine

A solution of benzyloxycarbonyl chloride (170 ml) in toluene (500 ml) is added dropwise to a solution of valienamine (100 g) and sodium hydrogen carbonate (100 g) in water (1 l) at 5°-10° C. while stirring, followed by stirring at the same temperature for 1 hour and at room temperature for 3 hours. The reaction mixture is allowed to stand for 2 hours keeping the temperature below 10° C. The resulting white crystalline precipitate is collected by filtration, washed with water and toluene and dried in a desiccator under reduced pressure. The filtrate and washings are combined and shaken. The aqueous layer is separated and washed with toluene, adjusted to pH 5-5.5 with 2 N hydrochloric acid and concentrated to about 400 ml. The concentrate is allowed to stand overnight in a refrigerator. The second crop of crystalline precipitate of N-benzyloxycarbonylvalienamine is collected by filtration, washed with cold water and dried in a desiccator under reduced pressure. Total yield: 146 g.

Elemental analysis, for $C_{15}H_{19}NO_6$: Calcd. (%): C, 58.24; H, 6.19; N, 4.53. Found (%): C, 58.31; H, 6.17; N, 4.49.

$[\alpha]_D^{24}+121.7°$ (c=1, $H_2O$).

IR $\nu_{max}^{KBr}cm^{-1}$: 1690 (C=O).

NMR (DMSO-$d_6$) δ: 5.02 (2H, s), 5.46 (1H,d,J=5 Hz), 6.67(1H,d, J=8.5 Hz), 7.33(5H,s).

(b) 9-Bromo-6,7,8-trihydroxy-1-hydroxymethyl-3-oxo-2-oxa-4-azabicyclo[3.3.1]nonane A solution of bromine (75 g) in methanol (450 ml) is added dropwise to a solution of N-benzyloxycarbonylvalienamine (146 g) in methanol (1.2 l) at 0°-5° C. with stirring, and the mixture is stirred for 1 hour at the same temperature. The reaction mixture is concentrated under reduced pressure. Ethanol-ethyl acetate (1:10)(2.2 l) is added to the residue and allowed to stand overnight in a refrigerator. The resulting crystals are collected by filtration, washed with ethylacetate and petroleum ether successively and dried in a desiccator under reduced pressure to give 9-bromo-6,7,8-trihydroxy-1-hydroxymethyl-3-oxo-2-oxa-4-azabicyclo[3.3.1]-nonane (136 g), which is recrystallized from water.

Elemental analysis, for $C_8H_{12}NO_6Br.H_2O$: Calcd. (%): C, 30.39; H, 4.46; N, 4.43; Br, 25.28. Found (%): C, 30.31; H, 4.52; N, 4.40; Br, 25.38.

$[\alpha]_D^{24}+42.1°$ (c=1, $H_2O$).

IR $\nu_{max}^{KBr}cm^{-1}$: 1700 (C=O).

NMR($D_2O$)δ: 3.66 (1H,t,J=9.3 Hz), 3.93(1H,t,J=3.2 Hz), 3.95(1H,d,J=13 Hz), 4.14(1H,d,J=13 Hz), 4.18(1H,d,J=9.3 Hz), 4.34(1H,dd,J=3 and 9.3 Hz), ~4.75(1H, overlaps with HOD).

EXAMPLE 14

(a) N-tert-Butoxycarbonylvalienamine

To valienamine (10 g) dissolved in water (50 ml) is added dioxane (50 ml). tert-Butyl 4,6-dimethylpyrimidin-2-ylthiocarbonate (16.8 g) is added to the solution and the mixture is stirred for 18 hours at room temperature. The reaction solution is concentrated to dryness under reduced pressure. The residue is dissolved in water (200 ml), washed with ethyl acetate, concentrated to about 50 ml under reduced pressure, and allowed to stand overnight in a refrigerator. Resulting crystals are filtered off and washed with cold water. The filtrate and the washings are combined and chromatographed on a column of MCI Gel CHP20P (produced by Mitsubishi Chem. Ind., Ltd., Japan, 400 ml). The column is washed with water and then eluted with a water-80% aqueous methanol gradient. The eluate is concentrated under reduced pressure and chromatographed on a column of Amberlite CG-50 ($H^+$ form, produced by Rohm & Haas Co., U.S.A., 550 ml) using water as an eluent. The eluate containing the objective compound is concentrated under reduced pressure and lyophilized to give N-tert-butoxycarbonylvalienamine (12.5 g) as white powder.

Elemental analysis, for $C_{12}H_{21}NO_6$: Calcd. (%): C, 52.35; H, 7.69; N, 5.09. Found (%): C, 52.09; H, 7.93; N, 5.02.

$[\alpha]_D^{23}+128.2°$ (c=1, $H_2O$).

NMR($D_2O$)δ: 1.58 (9H,s).

(b) 9-Bromo-6,7,8-trihydroxy-1-hydroxymethyl-3-oxo-2-oxa-4-azabicyclo[3.3.1]nonane A solution of bromine (1.8 g) in methanol (200 ml) is added dropwise to a solution of N-tert-butoxycarbonylvalienamine (2.8 g) in methanol (30 ml) under cooling in an iced water bath, followed by stirring for 1 hour. The reaction mixture is concentrated under reduced pressure, and the residue is chromatographed on a column of MCI Gel CHP20P (produced by Mitsubishi Chem. Ind., Japan, 250 ml) using water as an eluent. The eluate is concentrated under reduced pressure and lyophilized to give white powder (2.5 g). Acetic acid (40 ml) is added to the white powder and the mixture is heated at 80°-90° C. for 30 minutes, followed by allowing to stand overnight at room temperature to give crystals of 9-bromo-6,7,8-trihydroxy-1-hydroxymethyl-3-oxo-2-oxa-4-azabicyclo[3.3.1]nonane (2.1 g).

Elemental analysis, for $C_8H_{12}NO_6Br$: Calcd. (%): C, 32.23; H, 4.06, N, 4.70; Br, 26.81. Found (%): C, 32.11; H, 4.19; N, 4.87; Br, 26.67.

EXAMPLE 15

6,7,8-Trihydroxy-1-hydroxymethyl-3-oxo-2-oxa-4-azabicyclo[3.3.1]nonane

Sodium borohydride (55 g) is added by portions to a solution of 9-bromo-6,7,8-trihydroxy-1-hydroxymethyl-3-oxo-2-oxa-4-azabicyclo[3.3.1]nonane (100 g) in water (1.3 l) at 25°-30° C. with stirring. After stirring for 2 hours at the same temperature, the reaction mixture is adjusted to pH 6-7 with acetic acid and concentrated to about 800 ml under reduced pressure. The concentrate is chromatographed on a column of activated carbon (4.8 l), and the column is washed with water (5 l) and eluted with 50% aqueous methanol. The eluate is concentrated under reduced pressure. Methanol (350 ml) is added to the residue and refluxed for 10-20 minutes to remove a methanol soluble by-product. The mixture is allowed to stand in a refrigerator overnight, and the resulting crystals are collected by filtration, followed by washing with cold methanol and drying in a desiccator under reduced pressure to give 6,7,8-trihydroxy-1-hydroxymethyl-3-oxo-2-oxa-4-azabicyclo[3.3.1]nonane (64 g).

Elemental analysis, for $C_8H_{13}NO_6$: Calcd. (%): C,43.83; H,5.98; N,6.39. Found (%): C,43.80; H,5.96; N,6.52.

$[\alpha]_D^{24} + 35.0°$ (c=1, $H_2O$).

IR $\nu_{max}^{KBr}$ cm$^{-1}$: 1670 (C=O).

NMR ($D_2O$) δ: 2.07(1H,dd,J=2 Hz and 15 Hz), 2.34(1H,dd,J=5 Hz and 15 Hz), 3.45-4.1(6H).

mp 254°-255° C.(dec.).

EXAMPLE 16

9-Iodo-1-hydroxymethyl-6,7,8-trihydroxy-3-oxo-2-oxa-4-azabicyclo[3.3.1]nonane (a) A solution of N-benzyloxycarbonylvalienamine (3.1 g) obtained in Example 13(a) in methanol (50 ml) and a solution of iodine (2.6 g) in methanol (20 ml) are simultaneously added to methanol (20 ml) under cooling at 5°-10° C. The reaction mixture is stirred for 25 hours at room temperature and concentrated under reduced pressure. The residue is partitioned between ethyl acetate and water. The aqueous layer is separated, washed with ethyl acetate, and concentrated under reduced pressure. The residue is chromatographed on a column of MCI Gel CHP20P (produced by Mitsubishi Chem. Ind., Ltd., Japan, 250 ml) using water as an eluent. The eluate, containing the objective compound is concentrated under reduced pressure and lyophilized to give 9-iodo-1-hydroxymethyl-6,7,8-trihydroxy-3-oxo-2-oxa-4-azabicyclo[3.3.1]nonane (1.1 g).

(b) A solution of iodine monochloride (1.7 g) in acetonitrile (20 ml) is added dropwise to a solution of N-benzyloxycarbonylvalienamine (3.1 g) obtained in Example 13(a) in methanol (50 ml) under cooling at 0°-5° C. The mixture is stirred for 5 hours at 0°-5° C. and for 15 hours at room temperature. The reaction mixture is concentrated under reduced pressure and the residue is partitioned between ethyl acetate and water. The aqueous layer is separated, washed with ethyl acetate, adjusted to pH 5 with saturated sodium hydrogen carbonate solution, and concentrated under reduced pressure. The residue is chromatographed on a column of MCI Gel CHP20P (produced by Mitsubishi Chem. Ind., Ltd., Japan, 250 ml) using water as an eluent, and the eluate containing the objective compound is concentrated under reduced pressure. The residue is dissolved in hot water, and allowed to stand overnight in a refrigerator to give crystals of 9-iodo-1-hydroxymethyl-6,7,8-trihydroxy-3-oxo-2-oxa-4-azabicyclo[3.3.1]nonane (3.1 g).

Elemental analysis, for $C_8H_{12}NO_6I.H_2O$: Calcd. (%): C, 26.46; H, 3.89; N, 3.86. Found (%): C, 26.57; H, 3.97; N, 3.96.

$[\alpha]_D^{24} + 37.5°$ (c=1, $H_2O$).

IR $\nu_{max}^{KBr}$ cm$^{-1}$: 1680 (C=O).

NMR ($D_2O$) δ: 3.70 (1H,t,J=9.5 Hz), 3.92 (1H,t,J=3.5 Hz), 4.02 and 4.28(1H each,d,J=15 Hz), 4.33(1H,d,J=9.5 Hz), 4.53(1H,dd,J=3.5 Hz and 9 Hz), 4.79(1H,d,J=3.5 Hz).

EXAMPLE 17

1L(1S)-(1(OH),2,4,5/1,3)-5-Amino-1-hydroxymethyl-1,2,3,4-cyclohexanetetrol (Valiolamine)

Barium hydroxide (200 g) is added to a solution of 6,7,8-trihydroxy-1-hydroxymethyl-3-oxo-2-oxa-4-azabicyclo[3.3.1]nonane (50 g) in water (1.5 l). The mixture is heated at 70°-80° C. for 3 hours while stirring. The reaction mixture is cooled to room temperature, and carbon dioxide gas is bubbled into the mixture. The precipitate is filtered off and washed with water, and the filtrate and washings are combined and allowed to be adsorbed on a column of Amberlite CG-50 ($NH_4^+$ form, produced by Rohm & Haas Co., U.S.A., 1.6 l). The column is washed with water (1 l) and eluted with 0.2 N ammonia water. The eluate is concentrated to about 200 ml under reduced pressure and rechromatographed on a column of Dowex 1×2 ($OH^{31}$ form, produced by Dow Chem. Co., U.S.A. 1.6 l) by the use of water as a developing solvent. The eluate containing the objective compound is concentrated under reduced pressure and lyophilized to give valiolamine (42.7 g) as white powders.

Elemental analysis, for $C_7H_{15}NO_5.H_2O$: Calcd. (%): C, 39.80; H, 8.11; N, 6.63. Found (%): C, 39.87; H, 8.13; N, 6.68.

$[\alpha]_D^{25} + 19.6°$ (c=1, $H_2O$).

NMR ($D_2O$) δ: 1.80 (1H,dd,J=3.8 and 15.5 Hz), 2.07(1H,dd,J=3 and 15.5 Hz), 3.4-3.6(1H), 3.55(1H,d,J=10 Hz), 3.63(2H), 3.72(1H,dd,J=4.2 and 10 Hz), 3.99(1H,t,J=10 Hz).

$^{13}$C-NMR($D_2O$) δ: 33.5(t), 51.0(d), 66.3(t), 71.9(d), 74.5(d), 74.5(d), 76.8(s).

What is claimed is:

1. A compound of the formula

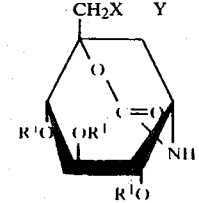

wherein X is hydroxyl group, a halogen or an acyloxy group; Y is hydrogen or a halogen; and OR$^1$ is an optionally protected hydroxyl group.

2. A compound as claimed in claim 1, wherein X is hydroxyl group; Y is hydrogen or a halogen; and OR$^1$ is hydroxyl group.

3. A compound as claimed in claim 1, wherein X is a halogen or an acyloxy group; and Y is hydrogen.

4. A compound as claimed in claim 1 or 2, namely 9-bromo-6,7,8-trihydroxy-1-hydroxymethyl-3-oxo-2-oxa-4-azabicyclo[3.3.1]nonane.

5. A compound as claimed in claim 1 or 2, namely 6,7,8-trihydroxy-1-hydroxymethyl-3-oxo-2-oxa-4-azabicyclo[3.3.1]nonane.

6. A compound as claimed in claim 1 or 3, namely 6,7,8-triacetoxy-1-iodomethyl-3-oxo-2-oxa-4-azabicyclo[3.3.1]nonane.

7. A compound as claimed in claim 1 or 3, namely 6,7,8-triacetoxy-1-acetoxymethyl-3-oxo-2-oxa-4-azabicyclo[3.3.1]nonane.

8. A process for producing a compound of the formula

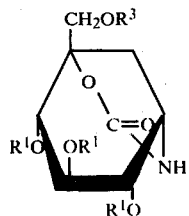

wherein $OR^1$ is an optionally protected hydroxyl group, and $OR^3$ is an acyloxy group, which comprises reacting a compound of the formula

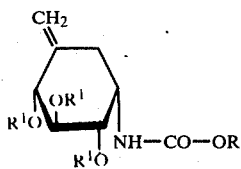

wherein R is an alkyl, aryl or aralkyl group; and $OR^1$ is as defined above:

with a halogenating agent to afford a compound of the formula

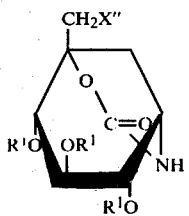

wherein $X''$ is a halogen; and $OR^1$ is as defined above;

then reacting the resultant compound with an acyloxylating agent.

9. A process for producing a compound of the formula

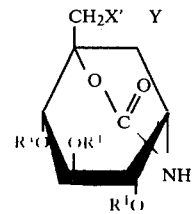

wherein $X'$ is a hydroxyl group; Y is a halogen, and $OR^1$ is an optionally protected hydroxyl group, which comprises reacting a compound of the formula

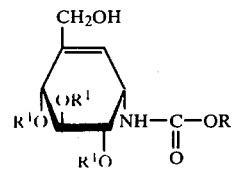

wherein R is an alkyl, aryl or aralkyl group; and $OR^1$ is as defined above; with a halogenating agent and removing, if necessary, a protective group.

10. A process according to claim 9 wherein in the compound of the formula

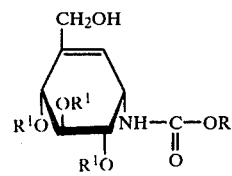

$OR^1$ is a hydroxyl group.

* * * * *